(12) United States Patent
Garvin et al.

(10) Patent No.: US 7,972,347 B2
(45) Date of Patent: Jul. 5, 2011

(54) DEVICE FOR SURGICAL REPAIR, CLOSURE, AND RECONSTRUCTION

(75) Inventors: Dennis D. Garvin, Roanoke, VA (US); Jeffrey P. Wong, Middleton, WI (US)

(73) Assignee: Surgical Security, LLC, Roanoke, VA (US)

( * ) Notice: Subject to any disclaimer, the term of this patent is extended or adjusted under 35 U.S.C. 154(b) by 1193 days.

(21) Appl. No.: 11/528,063

(22) Filed: Sep. 27, 2006

(65) Prior Publication Data

US 2007/0021779 A1    Jan. 25, 2007

Related U.S. Application Data

(63) Continuation-in-part of application No. 10/607,650, filed on Jun. 27, 2003, now abandoned.

(60) Provisional application No. 60/720,779, filed on Sep. 27, 2005.

(51) Int. Cl.
*A61B 17/08* (2006.01)
*A44B 17/00* (2006.01)

(52) U.S. Cl. .............. 606/151; 24/380; 24/DIG. 48; 606/157

(58) Field of Classification Search .......... 606/148, 606/150, 151, 205, 213, 215–218, 157, 74; 24/20 EE, 71 R, 311, 282, 284, 285, 24, 25, 24/20 CW, 20 TT, 380, DIG. 43, DIG. 48, 24/23 B, 16 PB; 600/37
See application file for complete search history.

(56) References Cited

U.S. PATENT DOCUMENTS

| | | | |
|---|---|---|---|
| 3,926,193 A | 12/1975 | Hasson | |
| 3,971,384 A | 7/1976 | Hasson | |
| 4,730,615 A | 3/1988 | Sutherland et al. | |
| 4,924,866 A | 5/1990 | Yoon | |
| 4,955,913 A * | 9/1990 | Robinson ................ | 606/228 |
| 5,342,376 A | 8/1994 | Ruff | |
| 5,584,859 A | 12/1996 | Brotz | |
| 6,176,868 B1 | 1/2001 | Detour | |
| 6,241,747 B1 | 6/2001 | Ruff | |
| 6,485,503 B2 | 11/2002 | Jacobs et al. | |
| 6,645,226 B1 | 11/2003 | Jacobs et al. | |
| 6,652,559 B1 | 11/2003 | Tetreault et al. | |
| 6,893,452 B2 | 5/2005 | Jacobs | |
| 2002/0058966 A1 | 5/2002 | Tormala et al. | |

* cited by examiner

*Primary Examiner* — Darwin P Erezo
*Assistant Examiner* — Melissa Ryckman
(74) *Attorney, Agent, or Firm* — Charles S. Sara, Esq.; DeWitt Ross & Stevens, S.C.

(57) ABSTRACT

A device and technique for a sutureless wound closure, which limits the risks of rupture and scarring, is described. The device includes a one-piece surgical fastener generally shaped in a curve along the width of the surgical fastener. The fastener includes a tissue insertion tongue with a plurality of tissue attachment points for fixing the fastener to skin tissue. The fastener also includes a clasp for engaging an identical surgical fastener. The surgical fastener can also be a two-piece structure including a male connecting strap and a female connector. Both pieces include a tissue-connecting mechanism for fixing to skin tissue. The female connector includes an engagement clasp for securing the male connecting strap to the female connector.

3 Claims, 13 Drawing Sheets

DEVICE FOR SURGICAL REPAIR, CLOSURE, AND RECONSTRUCTION

RELATED APPLICATIONS

This application is a continuation-in-part to U.S. patent application Ser. No. 10/607,650, filed Jun. 27, 2003, now abandoned in the name of Dennis D. Garvin, and entitled "Device for Sutureless Wound Closure," the contents of which are incorporated herein by reference.

This application claims priority to U.S. Provisional Patent Application No. 60/720,779, filed Sep. 27, 2005, in the names of Dennis D. Garvin and Jeffrey P. Wong, entitled "Device for Surgical Repair, Closure, and Reconstruction," the contents of which are incorporated herein by reference.

FIELD OF THE INVENTION

The present invention relates to a surgical fastener and technique for its use. Specifically, the invention is directed to a device to close wounds without the use of sutures.

DESCRIPTION OF THE PRIOR ART

Classical techniques to close wounds and incisions use sutures, basically using a needle and thread to sew the wound closed. While this technique acts to stitch the respective sides of the lesion together, it has several drawbacks. First, the tension required to pull the sides together is localized at the point of the stitch. This results in a tendency of the skin to tear around the stitch. Second, the skin may pouch out or sacculate between the stitches, greatly increasing the susceptibility of the wound to infection. Third, because the two sides of the wound are not evenly juxtaposed, scarring along the path of the sutures is increased. In addition, the placement of sutures requires deployment of needle and filament and afterward the tying off of the ends of the filament. This process is time consuming and requires workspace allowing dexterous manipulation.

Prior devices and techniques have been developed in an attempt to resolve these problems. These techniques range from superficial wound closure techniques to internal repair techniques. For example, U.S. Pat. No. 3,971,384 to Hasson describes a surgical closure device designed to bring the two edges of a wound or incision together. A piece of surgical tape is secured on each side of the wound. One piece of tape has an anchor for a tie strip secured to it while the other piece of tape has a slide secured to it. The tie strip has ratchet teeth on its dorsal surface such that the strip is inserted through the anchor end, across the wound and into the ratchet. The tape is then tightened and locked with the ratchet, bringing the two sides of the wound together. U.S. Pat. No. 4,924,866 to Yoon describes a device for closing wounds comprising two arms connected by a hinged joint. The arms have a single pair of "skin engaging members" on the ventral surface such that when the device is placed over the wound, the members enter the skin, pulling the wound together underneath the joint.

While the devices described by Hasson and Yoon are directed to sutureless methods of wound closure, they suffer from certain defects. In particular, Hasson is limited to superficial applications where the tape can stick and, further, by the strength and size of the tape. The described device can receive no more force from the opposing sides of the wound than the tape can hold. In addition, the size of the device is limited by the size of the tape. The device of Yoon is similarly handicapped. First, the device is limited in its pliability by the structure of the arms. Second, the device is limited in its wound closure ability due to the limited number of "skin engaging members" in relatively close proximity to the wound. Third, because there is no ratcheting element, the sides of the wound must first be properly juxtaposed and aligned before its insertion as there is no second chance for its deployment.

Other devices have been described for internal tissue repair or reconstruction. They include U.S. Pat. No. 6,241,747 to Ruff, which describes a barbed tissue connector for closing tissue wounds. The connector comprises an elongated shaft with pointed ends and a multitude of circumferentially placed barb-like points along the length of the shaft. The shaft has a midline with the barbs on either side pointing away from the midline and toward the respective ends. In use, the tip of one end is inserted into one side of the wound. The wound is spread apart and the other end of the device inserted. After each end is inserted into the wound, the tissue is pressed together with the fingers to fully engage the barbs and bring the sides of the lesion into express contact. Because the device of Ruff has no dorsal or ventral surface, it must be placed deep enough in the lesion such that the tip of the circumferential barbs remains within the skin. Such means of insertion adds to the trauma already experienced by the tissue.

U.S. Patent Application Publication 0058966 to Tormala et al. describes a surgical fastener or implant for repairing tissue wounds, particularly torn menisci in the knee. The invention comprises a shaft with an arrow-like point on one end and a blunted barb on the other end. The barbs on both ends of the shaft are directed such that they point toward the ends of the shaft, thereby facilitating insertion and discouraging its removal. The barbed end of the device is passed through both ends of the cartilage where the ends are locked onto the shaft by the inwardly pointed ridges of the blunt end. The device described by Tormala et al. requires use with a structure dense enough to have the device embedded within it and is thereby limited in its use.

U.S. Pat. No. 5,584,859 to Brotz is directed to a wound closure device for connecting tissue comprising integrated straps. The straps in Brotz are part of a whole, single device. The device, once constructed, essentially becomes a frame for immobilizing the wound tissue. The device encompasses two wound closure straps and a center body in one piece for holding the straps in place. The center body is necessary and integral to the closure device in Brotz.

U.S. Pat. No. 4,730,615 to Sutherland is directed to a sternum closure device with a head portion, a tail portion and a flexible spine portion. The tail portion is threaded through the sternum and brought back to a proximal head.

U.S. Pat. Nos. 6,893,452 to Jacobs and 6,645,226 and 6,485,503 to Jacobs, et al. are directed to surgical devices used to fixate soft tissue to both soft tissue and bone. The devices are meant to secure tissue to another fixed portion of tissue post-operatively. The devices include a plurality of attachment points connected to a backing that can be manipulated to close wounds, join soft tissue or bone, or create anastomoses. However, none of the patents disclose a device to close lacerations or wounds.

Furthermore, the prior art neither discloses nor contemplates a wound closure device using two straps or complementary wound closing devices that are pulled together to bring together the opposite sides of a wound.

SUMMARY OF THE INVENTION

The present invention is directed to a sutureless wound closure device that eliminates the pocketing and rupture associated with traditional sutures. Further, the device allows the tension, of pulling the opposing sides of the wound together, to be spread over a large area of the adjacent tissue. Also, the device is easy to use and does not further increase the trauma already experienced by the underlying tissue.

In a preferred embodiment, the invention comprises a wound closure device for connecting tissue comprising a first and second strap, each strap including a ventral barbed surface. The straps are adjustably connectable to one another, whereby the straps form a wound closure.

Specifically, the invention is directed to a wound closure device for connecting tissue comprising at least one pair of isolated first and second flexible straps wherein the first flexible strap has a proximal end with a male connector and a distal end, a ventral surface and dorsal surface. The second flexible strap has a proximal end with a female connector and a distal end, a ventral surface and a dorsal surface. The female connector is configured to adjustably connect to the male connector of the first strap, wherein the first strap and the second strap have at least one barb on the ventral surface for engaging the tissue.

The present invention is further directed to a method for closing a skin wound with a wound closure device, the device including at least one pair of isolated first and second flexible straps wherein the first flexible strap has a proximal end for the male connector and a distal end, and a ventral surface and a dorsal surface; and the second flexible strap has a proximal end with a female connector and a distal end, and a ventral surface and a dorsal surface, wherein the female connector is configured to adjustably connect to the male connector of the first strap, wherein the first strap and the second strap have at least one barb on the ventral surface for engaging the tissue and whereby the straps form a wound closure. The method is directed to placing the first strap and the second strap of the device on either side of the wound in an orientation generally perpendicular to the axis of the wound, wherein the second ends of each of the first and second straps are inserted into the surrounding skin of the wound, preferably the fascia, thereby situating the proximal ends of each of the first and second straps about the midline of the wound, such that the barbs of each of the first and second straps embed in the skin. The male connector is connected to the female connector of each of the first and second straps, and the straps are then adjusted to a desired tightness. Preferably, the female connector comprises a buckle, and the male connector comprises a ratcheted surface to accommodate the buckle.

The invention is also directed to a one-piece surgical fastener for connecting tissue comprising a tissue insertion tongue having an first upper side, a second lower side, a proximal end, a distal end, and at least one tissue attachment point; and an engagement clasp at the distal end of the tissue insertion tongue having a connecting mechanism for engaging a similar one-piece surgical fastener.

Further, the invention is directed to a surgical fastener system comprising at least one pair of separate, mating and identical one-piece surgical fasteners for connecting tissue, the surgical fasteners comprising a tissue insertion tongue having a first upper side, a second lower side, a proximal end, a distal end, and at least one tissue attachment point; and an engagement clasp at the distal end of the tissue insertion tongue having a connecting mechanism for engaging a similar one-piece surgical fastener.

The invention is also directed to a one-piece surgical fastener for connecting tissue comprising a tissue insertion tongue having an first upper side, a second lower side, a proximal end, a distal end; at least one tissue attachment point, wherein the at least one tissue attachment point has a base and a pointed end wherein the end of the tissue attachment point is directed to the proximal end of the tissue insertion tongue, wherein the tissue attachment point comprises a primary tissue attachment point and a secondary tissue attachment point wherein the secondary tissue attachment point extends from the primary tissue attachment point; and an engagement clasp at the distal end of the tissue insertion tongue having a connecting mechanism for engaging a similar one-piece surgical fastener, wherein the engagement clasp comprises a connecting area including an upper plate and a lower plate defining a cavity therein, wherein the connecting mechanism comprises at least one row of ratchets extending from the upper plate of the engagement clasp and at least one row of ratchets extending from the lower plate of the engagement clasp, wherein the ratchets are generally triangular in shape having a dorsal ridge ending in the cavity such that the dorsal ridge of the ratchets on the upper plate face the dorsal ridge of the ratchets on the lower plate.

The invention is further directed to a process of engaging a first and second surgical fastener for connecting a patient's tissue wherein the surgical fastener comprises a tissue insertion tongue having a first upper side, a second lower side, a proximal end, a distal end, and at least one tissue attachment point; and an engagement clasp having a first end at the distal end of the tissue insertion tongue and a second end, wherein the engagement clasp includes a connecting mechanism for engaging a similar one-piece surgical fastener, the process comprising: inserting the insertion tongue of the first surgical fastener into the skin layer of a patient; inserting the insertion tongue of the second surgical fastener into the skin layer of the patent such that the second ends of engagement clasps of the first and second surgical fasteners align; engaging the engagement clasps of the first and second surgical fasteners such that the connecting mechanisms of the first and second surgical fasteners are interconnected to prevent disengagement.

The invention is further directed to a surgical fastener for connecting tissue, comprising a male connecting strap having a proximal end, a distal end, and a tissue-connecting mechanism at the distal end; a female connector having a proximal end and a distal end and an engagement clasp at the proximal end and a tissue-connecting mechanism at the distal end, wherein the engagement clasp comprises a buckle for securing the male connecting strap.

The advantages of the invention are manifold. First, from a clinical standpoint, the invention helps to limit rupture of the wound. Second, from a cosmetic standpoint, the invention greatly limits scarring by reinforcing the subcutaneous fascia and eliminating sutures. Third, due to the above two advantages, the invention greatly reduces infection. Fourth, the invention is less painful and the patient heals faster than traditional wound closure methods because staples or sutures, piercing through the underlying muscle, are not required.

The device may be particularly advantageous for closing laparoscopic port sites, closing the sternum after cardiac surgery, and reinforcing traditional suture closings. Other applications include, but are not limited to, the restoration of damaged anatomy such as for stress incontinence and orthopedic repair of tendons and ligaments. Still other applications include, but are not limited to the moving, lifting, compressing, or reinforcing tissue for use in abdominoplasty, facelifts, breast lifts, and abdominal cinching. Some of these applications also pertain to animals.

The invention can also be used in most settings and locales from acute and field conditions to chronic conditions treated in care facilities. For example, the invention can be used for closure of small laparoscopy ports, which is difficult, particularly in obese patients. In these conditions, standard suturing through a small skin incision is very difficult and takes significant time or requires a larger skin incision to be made. Thus, the invention can make more demanding procedures easier and allow time-consuming procedures to be performed in more urgent situations.

The invention also allows greater blood flow to the healing tissue. When a conventional stitch is used under high tensions, it results in blood being cut off to the tissue encircled by the loop of the stitch. In contrast, by using the present invention, this problem is alleviated. Allowing greater blood flow to the incision reduces scarring and results in much better results, particularly with cosmetic surgery.

Further, the straps can be modified. Such modifications can allow the use of the invention in tightening waistlines, which have been stretched by injury, surgery or childbirth. The straps can also be applied to the top of a hernia repair to reduce risk of recurrence or adapted to facilitate a sternotomy closure, which would stabilize the chest and reduce discomfort after open-heart surgery.

The objects and advantages of the invention will appear more fully from the following detailed description of the preferred embodiment of the invention made in conjunction with the accompanying drawings.

BRIEF DESCRIPTION OF THE DRAWINGS

FIG. 2b is a partial ventral elevation view of the strap of FIG. 2a.

FIG. 4b is a ventral perspective view of the tissue-connecting strap of FIG. 4a.

FIG. 4c is a ventral plan view of the tissue-connecting strap of FIG. 4a.

FIG. 4d is a side elevation view of the tissue-connecting strap of FIG. 4a.

FIG. 4e is a dorsal elevated view of the tissue-connecting strap of FIG. 4a.

DETAILED DESCRIPTION OF THE INVENTION

Figure 1:
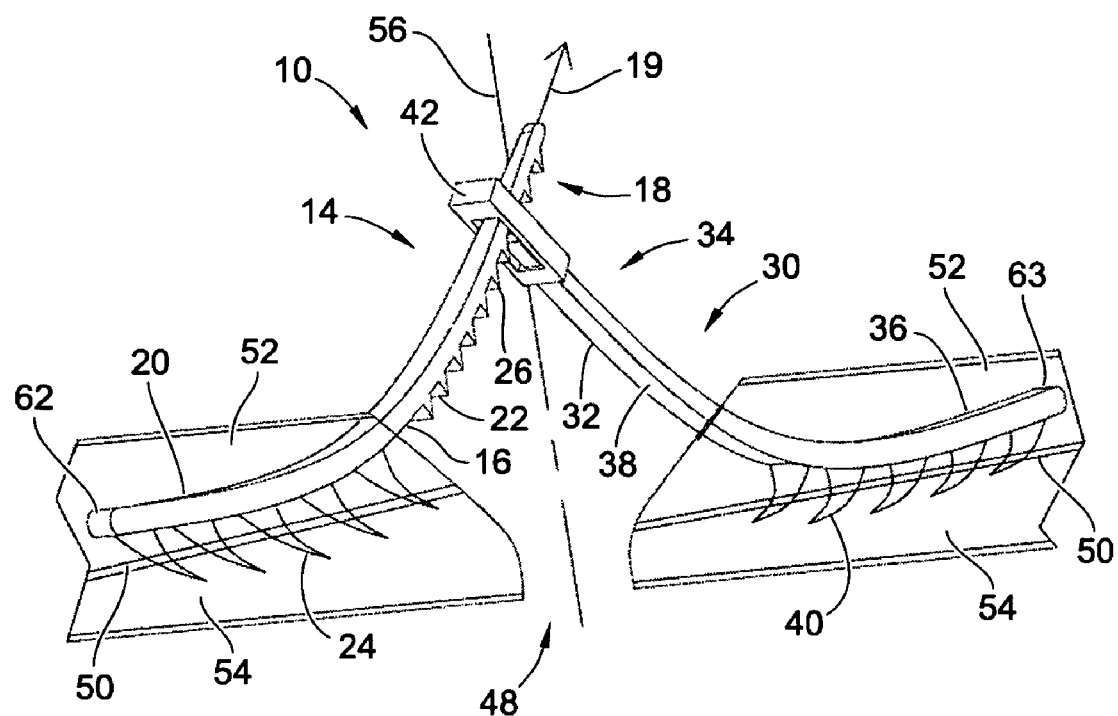
FIG. 1 is a perspective view of the first strap being inserted into the connector of the second strap and adjusted, thereby closing the wound.

Referring now to FIG. 1, there is illustrated a perspective view of a first embodiment of the disclosed invention 10. As illustrated, the invention 10 includes a first strap 14 and a second strap 30. The first strap 14 and the second strap 30 include distal ends 62 and 63 and proximal ends 18 and 34, respectively. The straps 14 and 30 are planar and made of a pliable material having dorsal surfaces 20 and 36 and a ventral surface 22 and 38. The dorsal surface 20 and 36 of the straps 14 and 30 are smooth while the ventral surfaces 22 and 38 include a plurality of tissue attachment points or small barbs 24 and 40 which project downward from the ventral surface 22 and 38 and curve toward the proximal end 18 and 34. In one preferred embodiment, the straps 14 and 30 have a length of about 4 cm and a width of about 0.5 cm. In other embodiments, the straps 14 and 30 may be larger or smaller to accommodate a wound, illustrated at 48. Although the shape of the straps 14, 30 may include planar sides as illustrated in FIG. 1, it is within the scope of the present invention for each strap to have a rounded configuration.

Figure 2A:
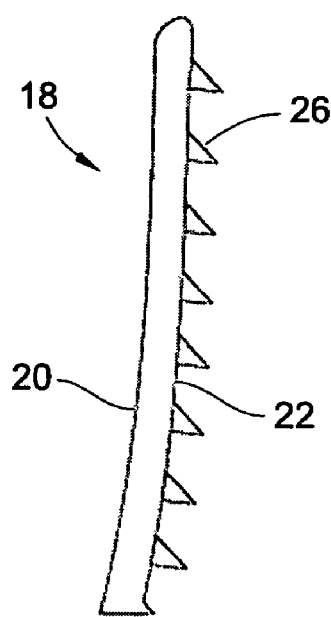
FIG. 2a is a partial side elevation view of the first strap of the device at the proximal end.
Figure 2B:
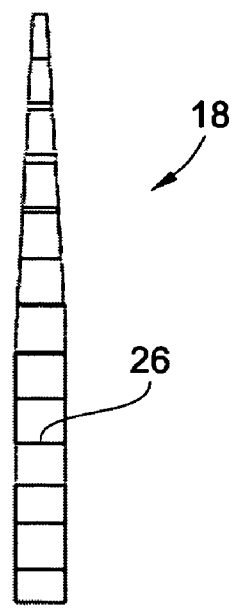

As shown in FIG. 1 and FIGS. 2a and 2b, the proximal end 18 of the first strap 14 is tapered along its planar sides, and the ventral surface 22 is composed of a plurality of small teeth or ratchets 26. The ratcheted surface may comprise about between 1 and 20 mm of the proximal end 18 of the first strap 14. Between the end of the ratcheted surface and the beginning of the barbs 24, there is a gap space 16 on the ventral surface 22, which is smooth and has no protuberances.

Figure 2C:
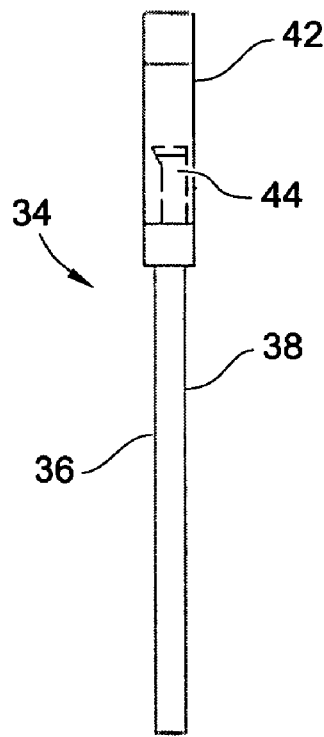
FIG. 2c is a partial side elevation view of the second strap of the device at the proximal end.
Figure 2D:
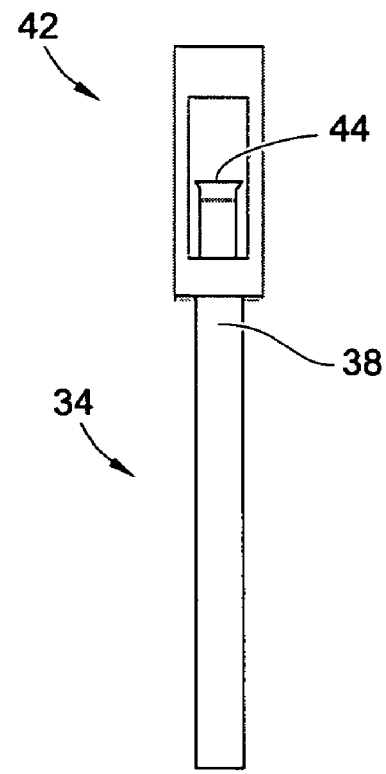
FIG. 2d is a partial ventral elevation view of the strap of FIG. 2c.

FIG. 1 and FIGS. 2c and 2d illustrate a preferred version of the second strap 30. In this version the proximal end 34 of the second strap 30 terminates in a buckle 42. However, in other versions, the proximal end 34 may terminate in any other form of connector, which may be capable of adjustably connecting the two straps such as VELCRO, adhesives or clips.

Between the buckle 42 and the most proximal of the barbs 40 is a gap space 32 marked by a smooth region of the ventral surface.

As illustrated in FIG. 1 the invention 10 is deployed in a lesion or wound 48. In use, the first strap 14 and the second strap 30 of the device 10 are placed on either side of the wound 48 in an orientation perpendicular to the axis of the wound 56. In a preferred embodiment, the straps 14 and 30 are inserted underneath the epidermis directly above the fascia 50 of the surrounding tissue. The distal end 62 and 63 of each strap 14 and 30 are directed away from the lesion while the proximal ends 18 and 34 of the straps 14 and 30 are situated at about the midline 56 of the wound 48. The straps 14 and 30 are displaced on either side of the wound 48 such that the gap space 16 and 32 of each strap 14 and 30 is generally behind the edge of the wound 48. The barbs 24 and 40 are then gently embedded in the underlying tissue, which in a preferred version of the invention is the fascia 50, so that the straps 14 and 30 engage the tissue.

FIG. 1 shows the barbs 24 and 40 of the straps 14 and 30 engaged in the fascia 50 with the barbs 24 and 40 pointed toward the midline 56 of the wound 48. The two straps 14 and 30 are connected at their proximal ends 18 and 34 and adjusted to a desired tightness. Illustrated is one preferred version of the invention showing the straps 14 and 30 that are tightened by pulling the proximal end 18 of the first strap 14 through the buckle 42 along the path designated by the arrow 19. The buckle 42 is then tightened by urging it distally on the ratchets 26 of the first strap 14. Tightening or putting tension on the proximal ends 18 and 34 of the straps 14 and 30 pulls the underlying fascia 50 of the wound together, allowing a smooth joining of the tissue surrounding the wound 48.

When the wound is large or the tissue is delicate, multiple straps 14 and 30 may be needed. When multiple straps are used, the straps 14 and 30 are deployed on either side of the wound 48. When all the straps 14 and 30 are deployed along the length of the lesion, the tapered, proximal end 18 of each first strap 14 is inserted into the buckle 42 of the respective second strap 30 until the locking tongue 44 engages the ratchets 26 of the first strap 14. In a particularly preferred version, the locking action of the first proximal end 18 in the buckle 42 is like that of a nylon tie such that once the tongue 44, illustrated in FIG. 2d, is engaged with the ratchets 26, the tension on the straps 14 and 30 can be increased by pulling the proximal end 18 through the buckle 42 in the direction of the arrow 19. The process of pulling the proximal end 18 of the first strap 14 through the buckle 42 of the second strap 30 of each of the respective first 14 and second 30 pair of straps, allows the opposing sides of the wound 48 to be brought close enough to begin tightening the individual straps in a sequential fashion until the opposing sides of the wound 48 are brought together.

Because the barbs 24 and 40 continue into the tissue surrounding the wound along the length of the straps 14 and 30, the tension loaded on the straps 14 and 30 is transferred to the underlying tissue assuring a smooth juxtaposition of the opposing sides of the wound 48. It will be appreciated that depending on the size of the wound 48, more or less straps 14 and 30 may be needed. For example, a very large wound 48 will require a large number of straps 14 and 30 while a small wound 48 will require one or a few straps 14 and 30. Similarly, very delicate or visible tissue may require many small straps 14 and 30 while tough or concealed tissues may require fewer large straps 14 and 30.

As shown in FIG. 1, the barbs 24 and 40 are conical in shape, ending at a point. The barbs 24 and 40 are designed to be pliable yet have stiffness such that they can pierce tissues ranging from muscle to skin to fat. Such barbs can be made from nylon, plastics and resorbable polymers such as polyglycolic acid and poly-L lactic acid, for instance. The barbs 24 and 40 may have a slightly different shape, depending on the particular tissue to be used in. For example, straps to be used in adipose tissue 52 may have barbs 24 and 40 that are longer and broader because the tissue is soft while barbs 24 and 40 to be used in muscle 54 or connective tissue, such as the fascia 50, may be shorter and narrower because those tissues are tough, and the barbs 24 and 40 do not need to project far into the tissue to embed. Nevertheless, the barbs 24 and 40 should generally be about between 2.5 mm long and 4.0 mm long and have a circumference around the base of about 2-3 mm. Further, while one exemplary version of the invention has only one barb 24 and 40 per row along the horizontal axis of the straps 14 and 30, in other exemplary versions, there may be several barbs 24 and 40 per row arranged along the ventral surface 22 and 38 of the straps 14 and 30.

FIGS. 2a-d illustrate a particularly preferred version of the proximal ends 18 and 34 of the first and second straps 14 and 30. FIGS. 2a and 2b show a side and ventral elevation, respectively, of the proximal end 18 of the first strap 14. As shown, the first strap 14 is tapered toward the proximal end 18 and has a series of small ratchet-like protrusions 26 on its ventral surface 22 while the dorsal surface 20 is flat. FIGS. 2c and 2d show a side and ventral elevation, respectively, of the proximal end 34 of the second strap 30. FIG. 2c shows the dorsal surface 36 and the ventral surface 38 with the buckle 42 terminating the proximal end 34 of the second strap 30. FIG. 2d illustrates the ventral surface 38 of the proximal end 34 of the second strap 30 with the buckle 42 terminating the proximal end and a locking tongue 44 situated within the buckle 42.

Figure 3A:
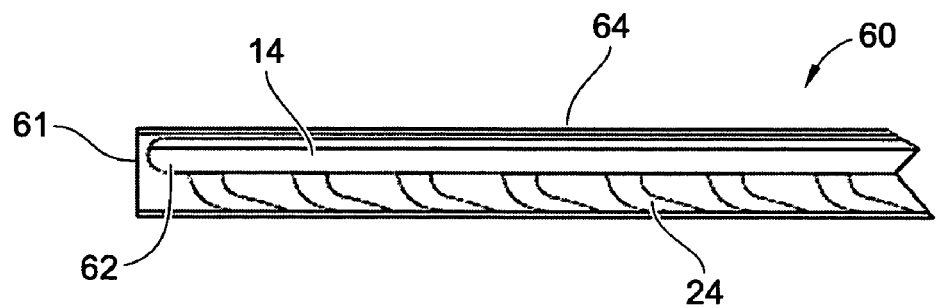
FIG. 3a is a partial side elevation view illustrating the flexion of the barbs of the closure device while stored in a trochar.

Methods to aid in deployment of the invention 10 are also included. For example, FIG. 3a illustrates the strap 14 inside a trochar 60. For the purposes of the drawing, only the second strap 14 is illustrated. However, both the first strap 14 and the second strap 30 are deployed with the trochar 60 and will have similar dimensions with comparable distal ends 62 and 63 as shown in FIG. 1. The trochar 60 is a cylindrical tube having walls 64 fabricated from a material stiff enough to use as an applicator. In particularly preferred versions, the trochar 60 may be made of, plastic or metal and will have a diameter slightly greater than the width of the straps 14 and 30 it is used to deploy. While in the trochar 60, the barbs 24 and 40 are flexed upward due to the slightly greater length of the barbs compared to the height of the trochar 60. The trochar 60 may serve both to store the straps 14 and 30 in and as an applicator for the straps 14 and 30. In situations where the trochar 60 is disposable, the straps would come stored in the trochar. In situations where the trochar 60 is reloadable, the straps 14 and 30 and the trochar 60 may be stored separately.

Figure 3B:
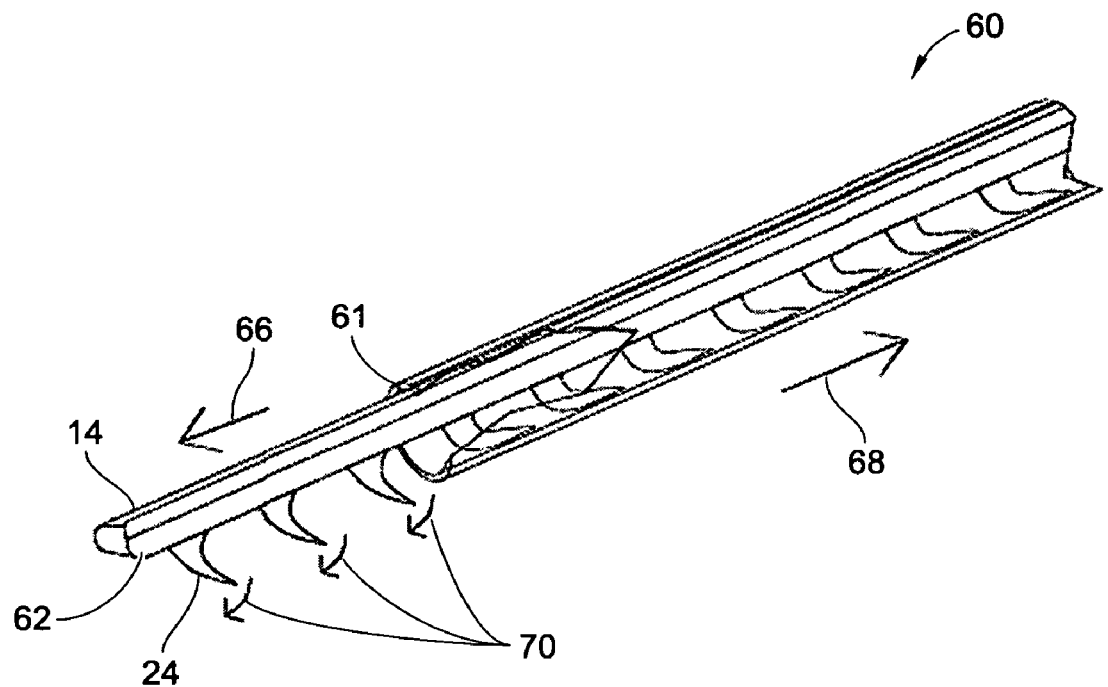
FIG. 3b is a partial perspective view of the device being deployed out of the trochar, shown in a cut-away view, with the barbs of the device being unflexed.

FIG. 3b illustrates the movement of the barbs 24 and 40 downward, shown by the arrows 70, as the straps 14 and 30 are slid out of the opening 61 of the trochar 60. In a preferred version of the invention, the straps 14 and 30 are deployed by sliding the end of the trochar 60 containing the distal end 62 of the strap 14 and 30 between the fascia 50 and the overlying adipose layer 52 of the tissue of the wound 48 (shown in FIG. 1). The distal ends 62 or 63 of the straps 14 or 30 are then urged out of the trochar 60 from the proximal end 18 or 34 in the direction of the arrow 66, deploying the most distal barbs 24 and 40 into the fascia 50. The trochar 60 is then pulled off the remainder of the strap 14 or 30, in the direction of the arrow 68, embedding the barbs 24 and 40 in the underlying fascia 50. This process is repeated for the opposing strap such that the proximal end 18 of the first strap 14 and the proximal end 34 of the second strap 30 abut each other at about the midline 56 of the wound 48. The proximal end 18 of the first strap 14 is then inserted in the buckle 42 of the second strap and tightened by pulling the first strap 14 in the direction of the arrow 19 as previously described.

It is a further facet of the invention 10 that while, in a preferred embodiment, the straps 14 and 30 are deployed subcutaneously in the fascia 50, as shown in FIG. 1., the straps may also be deployed on the surface of the skin with the barbs 24 and 40 engaged with the epidermis. The straps 14 and 30 may also be used internally in most situations where conventional stitches are used such as during exploratory surgery or resections, and with most tissues, including connective tissues, such as tendons, cartilage, ligaments and adipose tissue.

It is yet another facet of the invention 10 and of the other embodiments described in this disclosure that the straps 14 and 30 are made out of any hypoallergenic material and may be resorbable or permanent. In some instances, the straps 14 and 30 may not be resorbable and will remain engaged in the lesion or wound 48, such as permanent sutures are, or until the care provider elicits their removal. In other versions of the invention, the straps may be made of resorbable materials such as those described in U.S. Pat. No. 4,968,317 to Tormala et al. or U.S. Pat. No. 4,898,186 to Ikada et al., both hereby incorporated by reference for their description of such materials.

Reference is now made to FIGS. 4-9 for a second embodiment of the invention, which is directed to a wound closure device including a tissue-connecting strap 100 for connecting wound tissue. Advantageously, the tissue-connecting strap 100 can act upon itself thereby eliminating the necessity of mating straps of different configurations. Referring now to FIGS. 4a-f, the tissue-connecting strap 100 is a one-piece unit sectioned into a tissue insertion tongue 102 at the proximal end 106 of the tissue-connecting strap 100 and a forked or U-shaped engagement clasp 104 at the distal end 108 of the tissue-connecting strap 100. The insertion tongue 102 is defined by an upper side 110, which is generally smooth and preferably slightly curved. The lower side 112 is again generally smooth, but is defined by a series of attachment points or barb elements 114 having a base connected to the lower side and a pointed end. Although the figures illustrate ordered rows of barb elements 114 beginning at the distal end 106 and continuing along the lower side 112 of the tissue-connecting strap 100, it is within the scope of the present invention to have at least one barb element on the lower side 112 and more barbs than illustrated in the figures. In addition, the barb elements 114 may be present in precise rows of one, two, three or more barbs 114 as illustrated in the figures or the barb elements 114 may be presented in a staggered configuration. As best illustrated in FIG. 4c, the barb elements 114 include a primary barb 116 in which the end of the barb is directed toward the proximal end 108 of the tissue-connecting strap 100. The purpose of the primary barb 116 is to assist the securing of the tissue-connecting strap 100 in the fascia or skin area. Additionally, there is contemplated a secondary barb 118, generally smaller than the primary barb and pointing in the general direction of the distal end 106. The primary purpose of the secondary barb 118 is to assist in the "setting" of the tissue-connecting strap 100 in the skin tissue and to prevent the tissue-connecting strap 100 from backing out of the tissue in an opposite direction once the strap 100 has been set in the tissue.

The engagement clasp 104 is integrally connected to the insertion tongue 102 and is generally U-shaped with an upper side 120, a lower side 122 and a connecting side wall 124. The side 126 opposite the side wall 124 is open, defining a cavity 128. In addition, there is a cut-away area 130 on the lower side 122 of the engagement clasp 104 to assist in the engagement operation of two tissue-connecting straps 100.

Figure 4A:
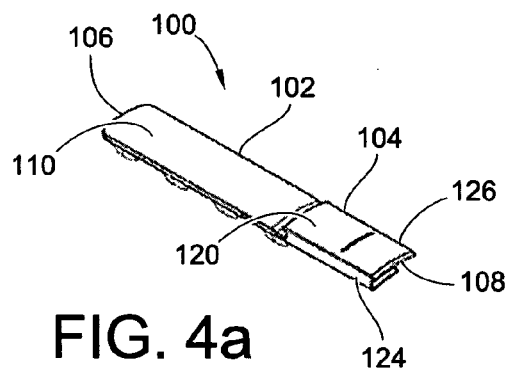
FIG. 4a is a dorsal perspective view of a second embodiment of a tissue-connecting strap of the present invention.
Figure 4B:
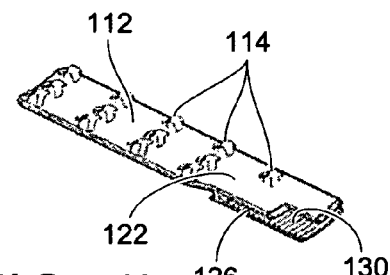
Figure 4C:
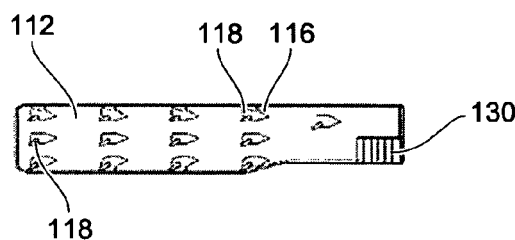
Figure 4D:
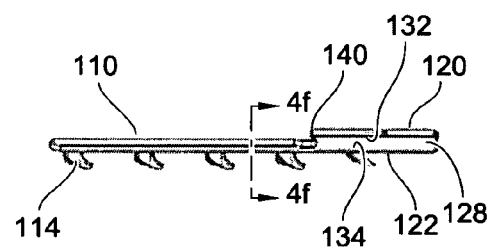
Figure 6:
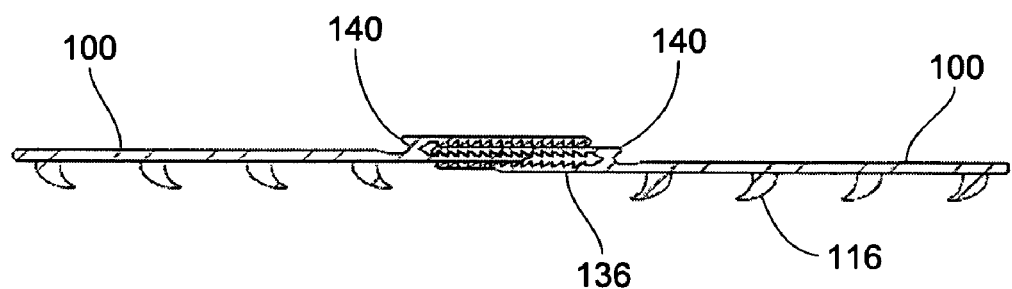
FIG. 6 is a side elevated view showing two tissue-connecting straps joined together taken at lines 6-6 of FIG. 5.

Referring more specifically to FIGS. 4b, 4c and 6, the upper interior wall 132 and lower interior wall 134 are defined by a plurality of small teeth or ratchets 136 which are there for the purpose of engaging a paired tissue connecting strap 100 in a manner to be described further on. The ratchets 136 are disposed in horizontal configuration, extending from the side wall 124 to the opening 126 on both the upper interior wall 132 and lower interior wall 134. It is within the scope to include at least one row of ratchets 136 in the engagement clasp 104 area. Preferably, multiple rows of connecting mechanisms such as ratchets 136 are included to provide increased securing or gripping tension between the tissue-connecting straps 100 once engaged. In addition, while the ratchets 136 are generally triangular in shape with the dorsal ridge of the ratchet 136 ending in the cavity such that the dorsal ridge of the ratchets 136 on the upper interior wall 132 face the dorsal ridge of the ratchets 136 on the lower interior wall 134, the ratchets 136 are preferably configured to lean or extend in the direction of the distal end 106 of the tissue-connecting strap 100 in order to increase the engagement tension of two tissue-connecting straps 100 once engaged.

While ratchets 136 are the preferred connecting mechanisms, it is within the scope of the present invention to provide alternative connecting mechanisms herein. Non-limiting examples of engaging devices include light curing epoxy including the entire electromagnetic spectrum from gamma rays, x-rays, ultraviolet, visible, infrared, microwave radio waves to ultra low frequencies for permanently or temporarily connecting the two straps; DC electrical curing epoxy for permanently or temporarily connecting two connecting straps; magnetic forces to bond the straps permanently or temporarily; ultrasonic energy to bond the straps permanently or temporarily; vibration energy to bond the straps permanently or temporarily; heat, including conduction, convection and radiation forces to bond straps permanently or temporarily; and adhesives, glues, epoxy using either a pressure force or a chemical reaction to bond the straps permanently or temporarily.

Figure 4E:
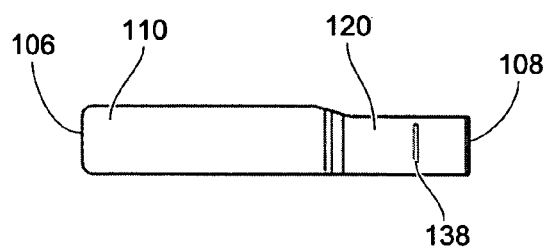
Figure 4F:
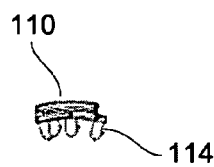
FIG. 4f is a cross-sectional view of the tissue-connecting strap taken at lines 4f-4f in FIG. 4d.

Referring to FIG. 4f, the shape of the width of the tissue-connecting strap 100 is preferably generally curved in a concave fashion, as illustrated in FIG. 4f, to prevent accidental disengagement of the tissue-connecting strap 100 once the strap is placed in the skin tissue.

As illustrated in FIGS. 4a and 4e, there is also a midline marker 138 to assist in the proper engagement of two tissue-connecting straps 100.

Figure 5:
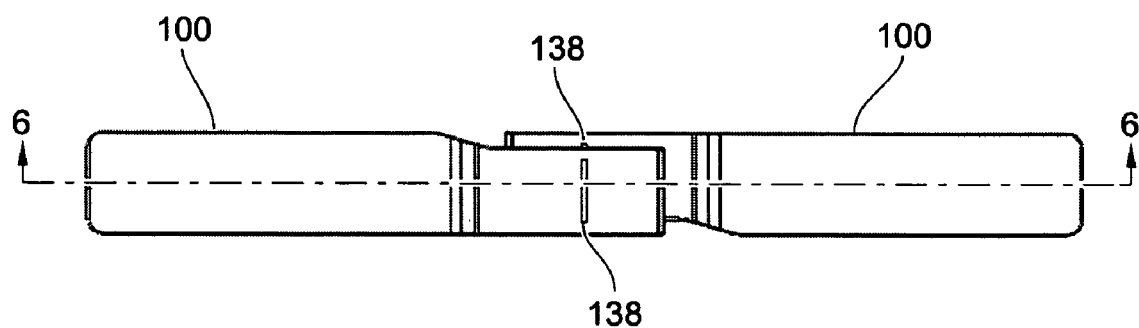
FIG. 5 is an elevated dorsal view illustrating two opposed tissue-connecting straps joined together.

Reference is now made to FIGS. 5-9 for a description of the process of engaging the tissue-connecting strap 100. As illustrated in FIGS. 5 and 6, two identical tissue-connecting straps 100 may be used for the wound closure device. In operation, the insertion tongue 102 is inserted into the skin layer (not shown), preferably in the fascia in similar fashion as is illustrated in FIG. 1, with the distal end 106 extending into the skin tissue layer. An identical tissue-connecting strap 100 is then placed on the opposite wall of the wound in similar fashion. Once the two tissue-connecting straps 100 are placed such that the proximal ends 108 are facing each other, the tissue-connecting straps 100 can be engaged for wound closure. Engagement can be achieved in at least two ways. First, the tissue-connecting straps 100 can be pressed together such that the openings 126 of each of the tissue-connecting straps 100 are facing each other somewhat in parallel alignment with the midline markers 138 of each of the tissue-connecting straps 100 also in alignment. The engagement clasp can then be slidably inserted upon each other through the openings 106 such that the ratchets 136 of each of the tissue-connecting straps 100 engage upon each other, thereby preventing disengagement by forces pulling at the distal ends 106 of each of the engaged connecting straps. The curved structure of the tissue-connecting straps 100 and the side walls 124 act to prevent lateral disengagement of the tissue-connecting straps 100. Although engagement is achieved when one or two rows of ratchets 136 are engaged, stronger engagement is achieved when all of the rows of ratchets 136 are engaged such that the midline markers 138 of each of the tissue-connecting straps 100 are in alignment as illustrated in FIG. 5.

As illustrated in FIG. 6, the configuration of engagement shows the ratchets 136 of the upper interior wall 132 of the right tissue-connecting strap 100 to be engaged with the ratchets 136 of the lower interior wall 134 of the left tissue-connecting strap 100. Because the tissue-connecting straps 100 are identical in configuration, the engagement can be reversed whereby the ratchets 136 of the upper interior wall 132 of the left tissue-connecting strap 100 is engaged with the ratchets 136 of the lower wall 134 of the right tissue-connecting strap 100 without any diminishing effect on the engagement.

Figure 7:
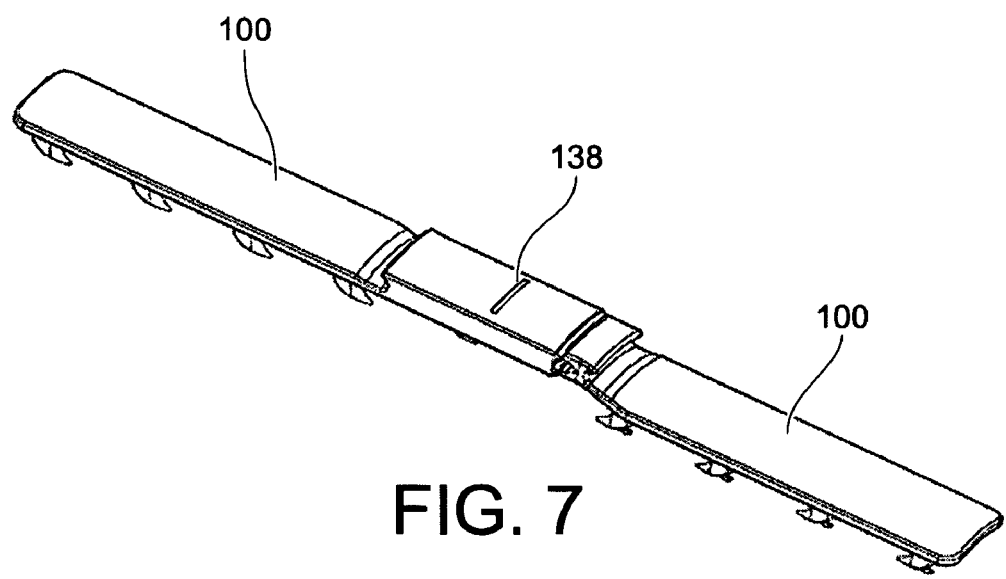
FIG. 7 is a dorsal perspective view showing two tissue-connecting straps joined together.
Figure 8:
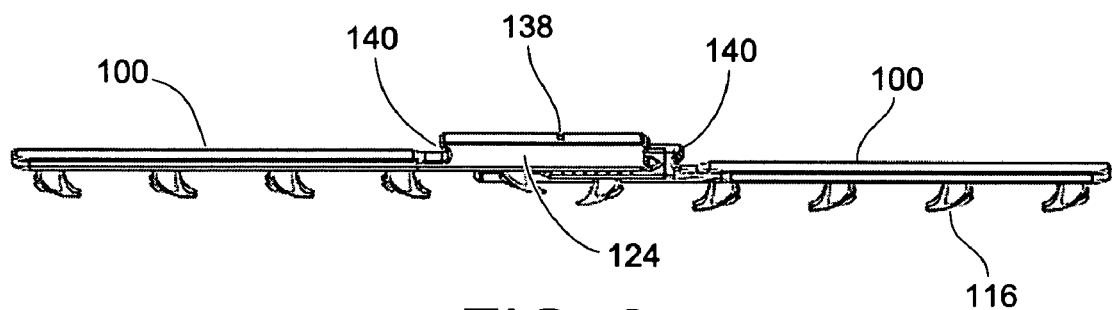
FIG. 8 is a side elevated view showing two tissue-connecting straps joined together.
Figure 9A:
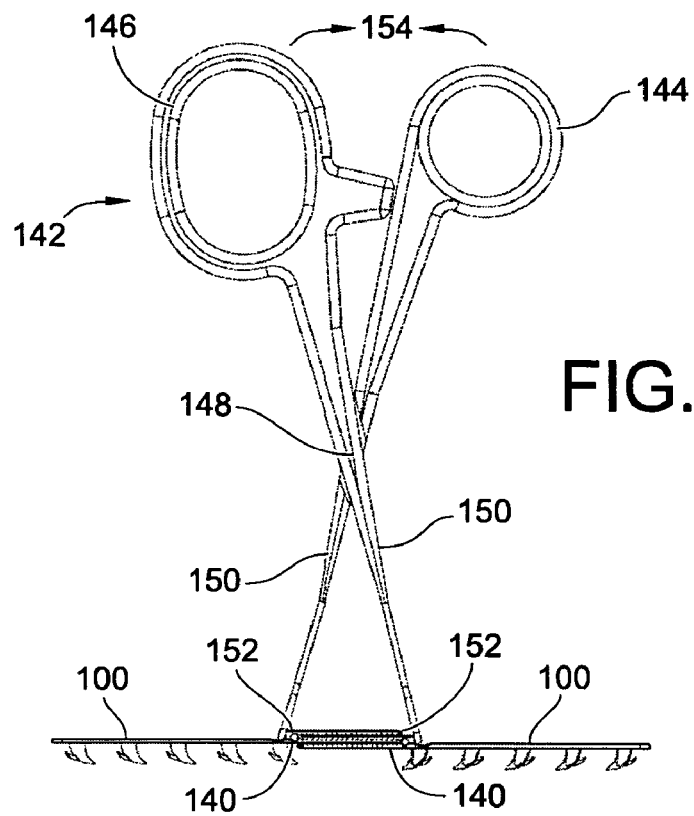
FIG. 9a is a side elevated view illustrating a strap closure device releasably connected to the two tissue-connecting straps.
Figure 9B:
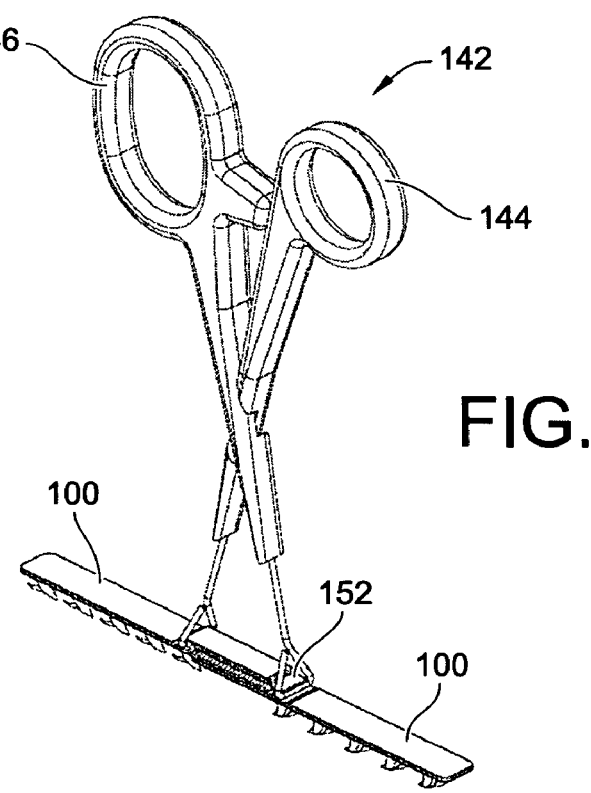
FIG. 9b is a perspective view illustrating the strap closure device releasably connecting the two tissue-connecting straps.

Reference is now made to FIGS. 7 and 8 for further illustrations showing the tissue-connecting straps 100 in complete engagement. Referring now to FIGS. 4d, 6, 8, 9a and 9b, the tissue-connecting strap 100 can be further defined by a tool engagement slot 140, which is a generally inwardly curved area between the upper side 110 of the insertion tongue 102 and the upper side 120 of the engagement clasp. As illustrated in FIGS. 9a and 9b, the present invention contemplates a wound closure system having two identical tissue-connecting straps 100 and an engagement tool 142. The contemplated engagement tool 142 has a typical scissors-shaped configuration with finger slots 144 and 146, a hinged joint 148 and extension arms 150. Situated at the distal end of the extension arms 150 are triangular hooks 152 for latching each of the two engagement slots 140 of the tissue-connecting straps 100. The hooks 152 of the engagement tool 142 grasp each tissue-connecting strap 100 at the tool engagement slot 140 in order to close the tissue-connecting straps 100 upon each other. As illustrated, the engagement tool 142 can easily gauge each of the tool engagement slots 140 of the separated tissue-connecting straps 100, even if misaligned, to bring the tissue-connecting straps 100 together in aligned engagement by bringing the finger slots 144 and 146 together in the direction of the arrows 154 until the midline markers 138 of each of the tissue-connecting straps 100 are in direct alignment.

Figure 10:
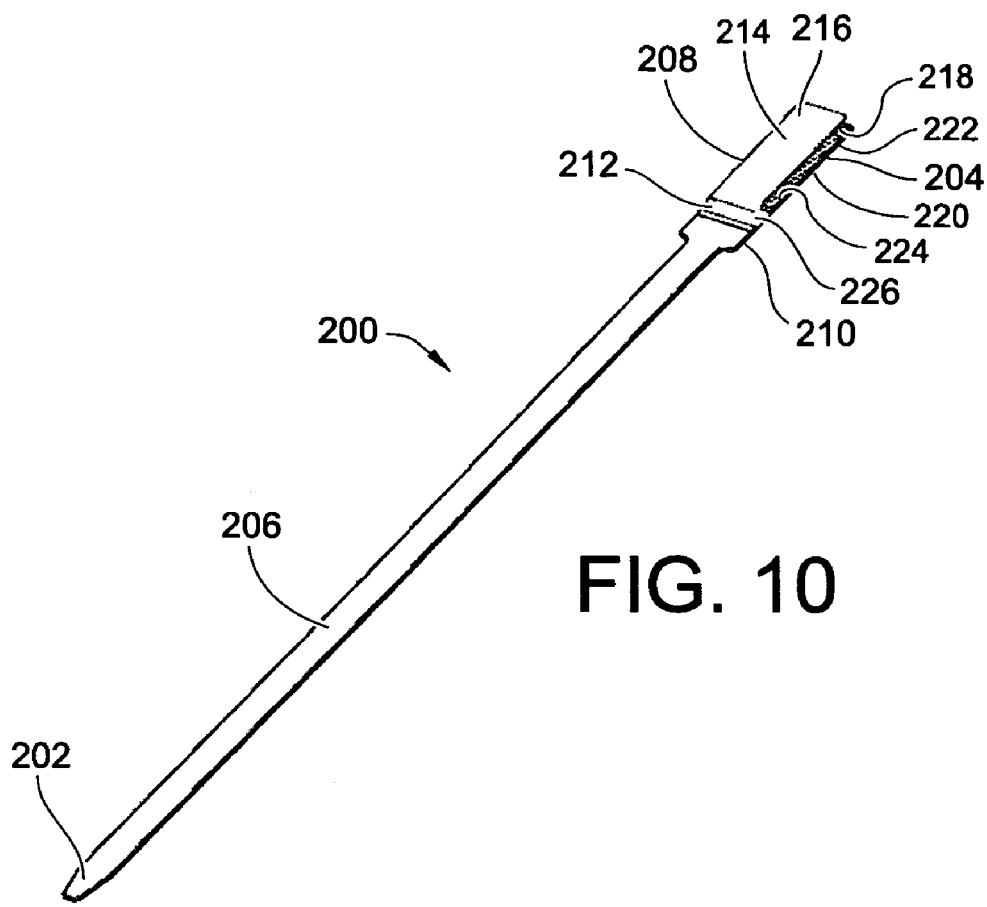
FIG. 10 is a perspective view of a third embodiment of a closure device illustrating the male connector strap.

Reference is now made to FIGS. 10-15 for a third embodiment of the present invention, which contemplates a wound closure device for connecting tissues. Unlike the second embodiment, the third embodiment includes a male connecting strap 200, as illustrated in FIG. 10, with a proximal end 202 and a distal end 204. As illustrated in FIG. 10, the proximal end 202 preferably has a tapered end. The male connecting strap 200 includes an elongated strap 206 and an engagement clasp 208 integrally connected at an area 210 which can be defined by the tool engagement slot 212 similar to the tool engagement slot 140 in FIG. 8 in the second embodiment.

The engagement clasp 208 is defined by forked opening consisting of an upper planar side 214 in which the outer wall 216 is generally smooth in configuration and the inner wall 218 includes ratchets similar to the rows of ratchets 136 in the second embodiment of this invention. Likewise, there is a lower planar side 220 in general parallel engagement with the upper planar side 214. The lower planar side 220 includes a generally smooth outer wall 222 and a ratcheted inner wall 224. The sides 214 and 220 remain in parallel engagement because of an end wall 226 defined by the tool engagement slot 212. Although not shown, it is within the scope of the present invention to provide the engagement clasp 208 with a side wall connecting the upper planar side 214 and the lower planar side 220, similar to side wall 124 illustrated in the second embodiment and FIG. 4a.

Figure 11:
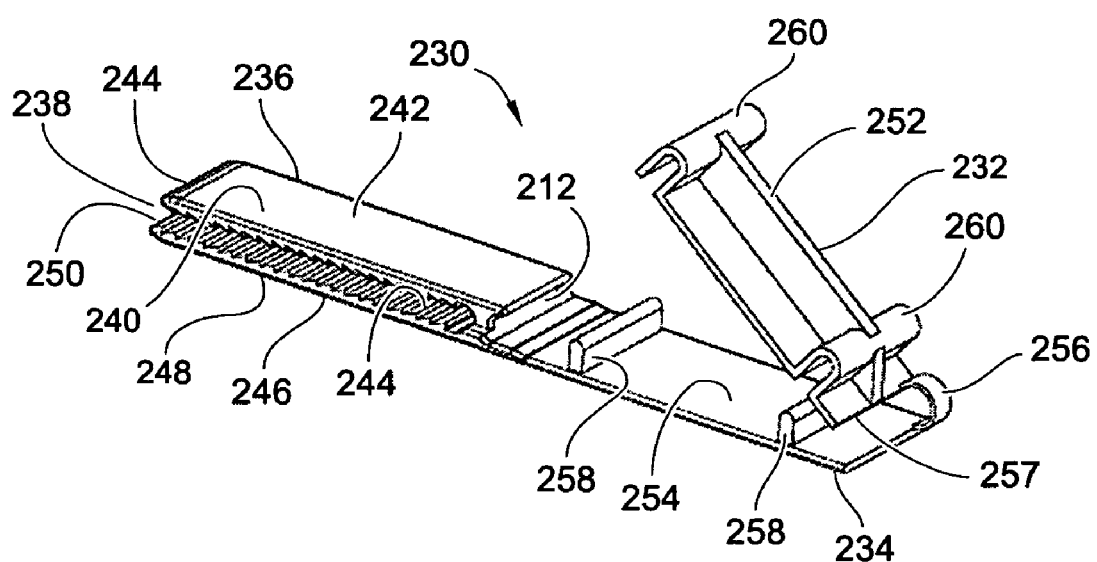
FIG. 11 is a perspective view illustrating the female connector adapted for use with the male connector strap of FIG. 10.

Illustrated in FIG. 11 is the female connector 230 defined by a hinged engagement clasp 232 at the proximal end 234 and the forked engagement clasp 236, which is similar in configuration to the engagement clasp 208 of the male connecting strap 200. Like the male connecting strap 200, the forked engagement clasp 236 is located at the distal end 238 of the female connector 230 and includes a tool engagement slot 212, an upper planar side 240, including a generally smooth outer wall 242, a ratcheted inner wall 244, a lower planar side 246 with a generally smooth outer wall 248 and a ratcheted inner wall 250.

As illustrated in FIG. 11, the hinged engagement clasp 232 is defined by a rotating hinge bar 252 rotatably connected to the receiving platform 254 by a hinge 256. Preferably, the hinge engagement clasp 232 is a one-piece extruded plastic or polymer material in which the hinge bar 252 is connected to the receiving platform 254 by a plastic memory hinge molded with the extruded device which allows the rotation of the hinge bar 252 from an open position as illustrated in FIG. 11 to a closed position. The receiving platform 254 is defined by one or more posts 258 which are designed to engage with a complementary post receptor 260 located on the hinge bar 252.

Figure 12:
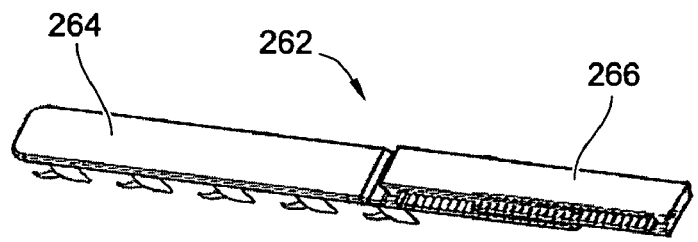
FIG. 12 is a dorsal perspective view of the tissue-connecting strap for use with the male connector strap and the female connector.
Figure 13:
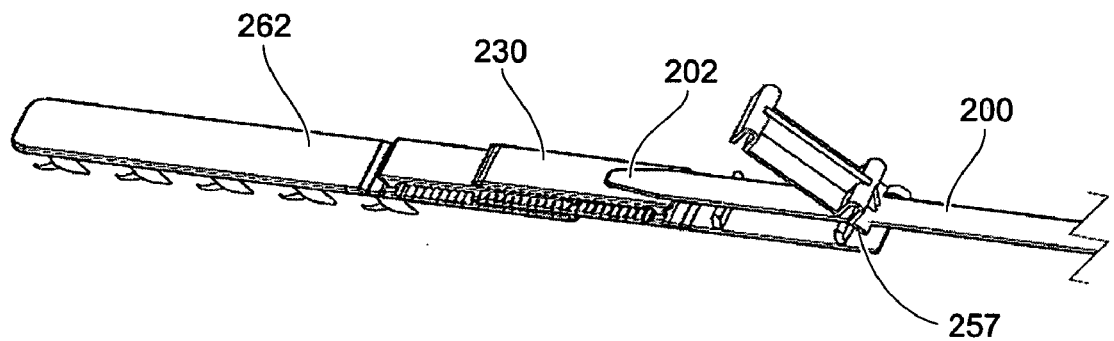
FIG. 13 is a partial dorsal perspective view illustrating the tissue connecting strap connected to the female adapter.
Figure 14:
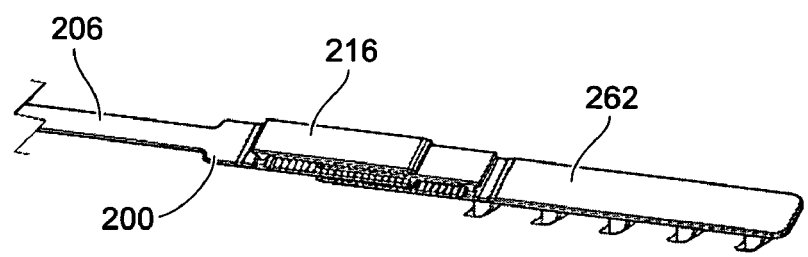
FIG. 14 is a partial dorsal perspective view illustrating the tissue connecting strap attached to the male connector strap.

Referring now to FIG. 12, there is illustrated a tissue-connecting strap 262 which is designed to engage either the engagement clasp 208 of the male connecting strap 200 or the engagement clasp 236 of the female connector 230. In either configuration, the tissue-connecting strap 262 is identical in structure. Therefore, the tissue-connecting strap 262 can be used for either the male connecting strap 200 or the female connector 230. The tissue-connecting strap includes a tissue insertion tongue 264 similar in shape and structure as the tissue insertion tongue 102 in the second embodiment and a forked engagement clasp 266 similar in shape and structure to the engagement clasp 208 and 236 of the male connecting strap 200 and female connector 230, respectively. As illustrated in FIGS. 13 and 14, the tissue-connecting strap 262 is first designed for placement into the tissue in similar fashion as that described with respect to the second embodiment. Once the tissue-connecting strap 262 is placed into the tissue at opposite sides of the wound, the female connector 230 engages the tissue-connecting strap 262, as illustrated in FIG. 13.

It is within the scope of the third embodiment to use an engagement tool 142 as illustrated in FIGS. 9a and 9b for engagement of the female connector 230 to the tissue-connecting strap 262. Likewise, and as illustrated in FIG. 14, the male connecting strap 200 engages the tissue-connecting strap 262 by similar means as described with respect to FIG. 13.

It is within the scope of the present invention to eliminate the tissue-connecting and the engagement clasps 208 and 236 of the male connecting strap 200 and female connector 230, respectively, in favor of a molded strap in which the male connecting strap 200 includes the tissue-connecting strap 262 integrally connected thereon and the female connector 230 includes the tissue-connecting strap 262 integrally connected thereon.

Once the male connecting strap 200 and female connector 230 are placed in the wound tissue, the proximal end 202 of the male connecting strap 200 is urged through the slot 257 in the hinge engagement clasp 232. The strap 200 can then continue to be pulled through the slot 257 to the desired tension. Once the desired tension is achieved, the hinge bar 252 can rotate such that the complementary post receptors 260 engage with the posts 258 on the receiving platform 254 thereby placing the male connecting strap 200 in locking engagement with the female connector 230. If desired, any extended portion of the male connecting strap 200 can then be removed by scissors or the like. In this manner, the female connector 230 and the tissue-connecting strap 262 of the male connecting strap 200 may be placed in remote locations on the patient's body.

In addition to the use of the male connecting strap 200 and the female connector 230, the present invention contemplates a variety of connecting mechanisms including, but not limited to: a buckle fixed to the first strap for mating with a ratchet fixed to the second strap similar to that disclosure with respect to the first embodiment; two strips of material, each attached to its respective strap for connection by twisting the strips together, thereby pulling the straps together; a button-in-hole assembly known to the art wherein a hitch is attached to one strap for engagement with one of a series of holes on the other strap; serration (one strap having a serrated end that is pulled through a fixation hole at the end of the other strap); knot tying first and second strips of material, each attached to its respective strap; a hook-and-loop fastener; a tapered nail with a head (brad) for holding the straps together; a string of pearl-like plastic beads on one strap for engagement with a lock ring on the other; entrapment with an eccentric cam; light curing epoxy including the entire electromagnetic spectrum from gamma rays, x-rays, ultraviolet, visible, infrared, microwave radio waves to ultra low frequencies for permanently or temporarily connecting the two straps; DC electrical curing epoxy for permanently or temporarily connecting the two straps; magnetic forces to bond the straps permanently or temporarily; ultrasonic energy to bond the straps permanently or temporarily; vibration energy to bond the straps permanently or temporarily; heat, including conduction, convection and radiation forces to bond straps permanently or temporarily; and adhesives, glues, epoxy using either a pressure force or a chemical reaction to bond the straps permanently or temporarily.

Figure 15:
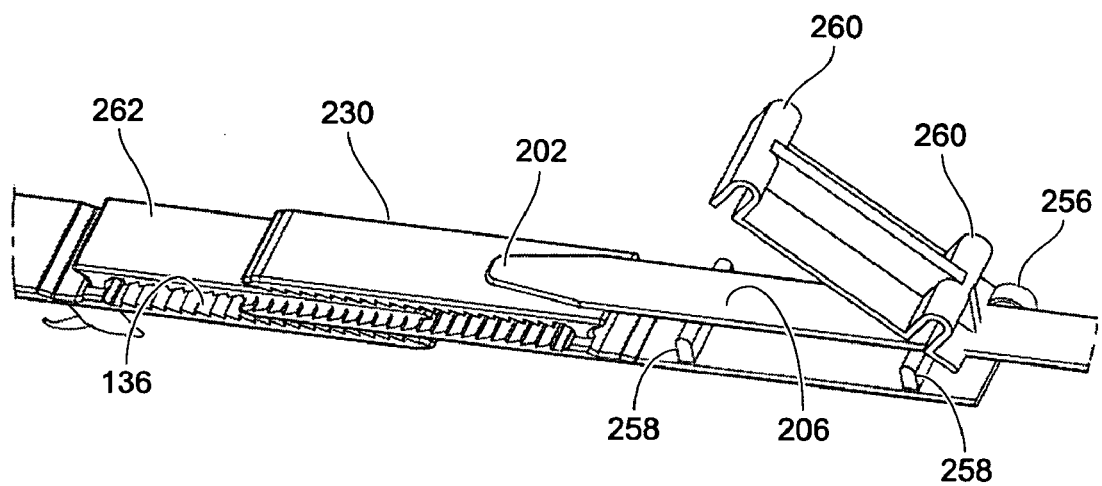
FIG. 15 is a partial dorsal perspective view illustrating the tissue-connecting strap connected to the female adapter, and the placement of the male connecting strap within the female connector.

Referring now to FIG. 15, there is illustrated a method for both coarse and fine adjustment of the length of the engagement strap 206. As illustrated in FIG. 15, the female connector 230 is placed in half engagement with the tissue-connecting strap 262 such that approximately one-half of the rows of ratchets 136 are in engagement as illustrated by the position of the distal end 235 of the female connector 230. In this manner, the proximal end 202 of the engagement strap 206 can be urged in a direction to and through the distal end 235 of the female connector 230 until desired tension is achieved on the engagement strap 206. Once desired tension is achieved, the hinge bar 252 is rotated upon its hinge 256 such that the host receptors 260 engage with the posts 258 thereby locking the engagement strap 206 in engagement with the female connector 230. Once this occurs, the end of the strap 206 can be trimmed if desired. If fine tune adjustment now needs to be made to increase the tension of the engagement strap 206, the engagement tool 142 (not illustrated in FIG. 15) can be placed on the tool engagement slots 212 in order to tighten the connection between the slots 212 thereby increasing the tension of the engagement strap 206.

It is within the scope of the present invention to have the engagement strap 206 of any desired length. Therefore, the female connectors 230 could feasibly be placed within the fascia area of the tissue in the front midline section of a patient. The male connecting strap 200 could then be engaged, by means of the tissue-connecting strap 262, along the back or spinal area of the patient. The engagement strap 260 could then extend around the torso of the patient, engage the female connector 230, be tightened to a desired tension, and locked in place with the desired tension remaining intact. As will be described later in this disclosure, the device of the third embodiment has a specific use not only for wound closures, but also for plastic surgery or facial or body augmentation.

Figure 16:
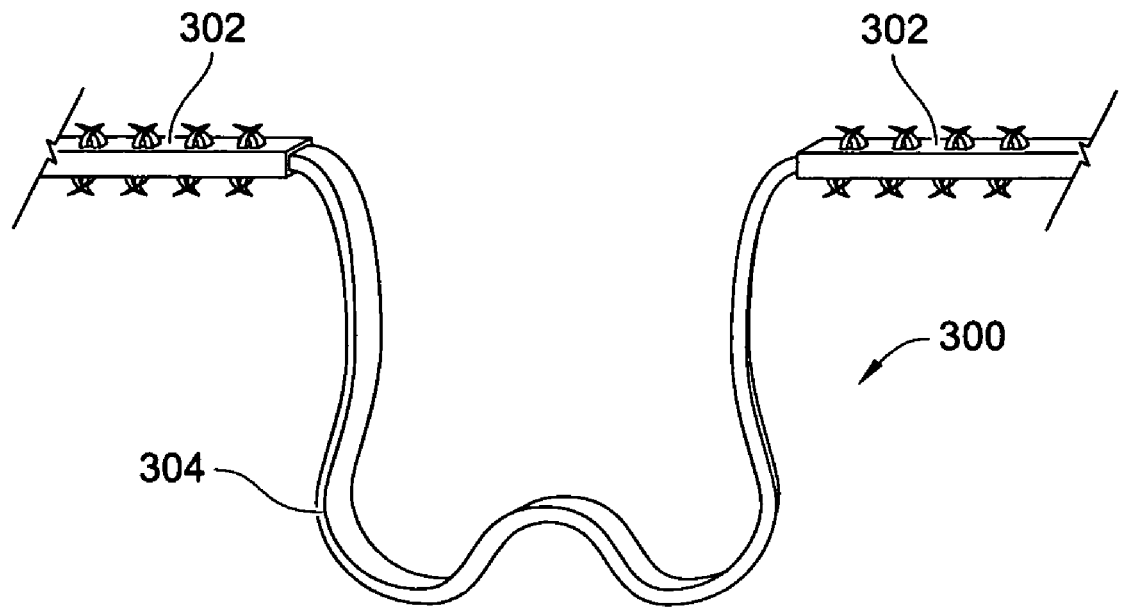
FIG. 16 is a side elevated view illustrating a fourth embodiment of the sutureless closure device.
Figure 17:
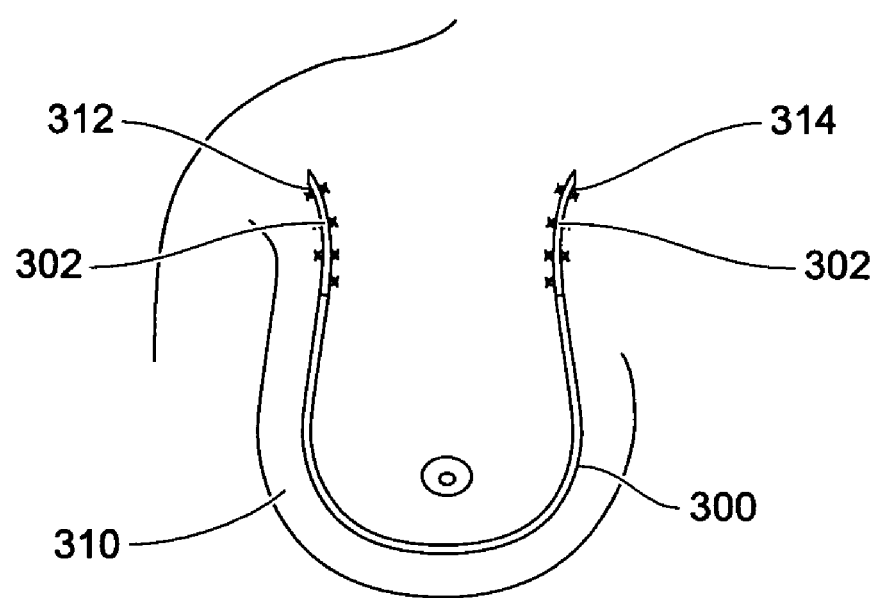
FIG. 17 is a front elevated view illustrating the use of the strap of FIG. 16 during breast augmentation.

Reference is now made to FIGS. 16-19 for examples of various uses of the wound closure devices of the present invention. Referring now to FIGS. 16 and 17, there is illustrated a system of using the device of the present invention for breast augmentation. Illustrated in FIG. 16 is a strap for use in plastic surgery, such as breast augmentation, abdominoplasty, or other procedures involving tightening or adding tension to various areas in the body. As illustrated in FIG. 16, the device is a one-piece strap 300, which includes tissue insertion tongues 302 at both ends of the strap 300. The tissue insertion tongues 302 are similar in shape and design as that described with reference to tissue insertion tongues 102 with respect to the second embodiment and illustrated in FIG. 4a. The tissue insertion tongues 102 are connected to each other by means of a flexible tape 304. It is within the scope of the present invention to provide a tape of any desired width, length, thickness or flexibility depending on the present needs. For example, the tape could be one-quarter inch in width or less up to and beyond one inch in width. Preferably, the tape is flexible and made of materials described herein. As illustrated in FIG. 17, the strap 300 is designed to be placed under the outer skin layer so that it will not be shown on the surface. In operation, one of the tissue insertion tongues 302 is placed in securing engagement in the fascia layer of the skin at a desired location designated at 312 above the breast 310. The tape 304 is then surgically placed beneath the skin layer of the breast in such a way as to engage the breast 310 for lifting. Tension is then placed on the tape 304 by raising the second tissue insertion tongue above the breast 310 in order to lift the breast 310 to the desired location. Once the desired location is achieved, the tissue insertion tongue is placed in securing engagement within the fascia layer of the skin at location 314.

While the tape 304, as illustrated in FIG. 16, is designed to be of a specific length, it is within the scope of the present invention to apply the system of the third embodiment such that the tape 304 is replaced by an engagement strap 206. In this manner, one of the tissue insertion tongues 302 would be replaced by a female connector 230 and tissue-connecting strap 262 combination. The other tissue insertion tongue 302 would be replaced by a male connecting strap 200 and tissue connecting strap 262 combination. In this manner, the engagement strap 206 can be of any indeterminate length. However, the length can be adjusted as described with respect to the second embodiment.

Figure 18:
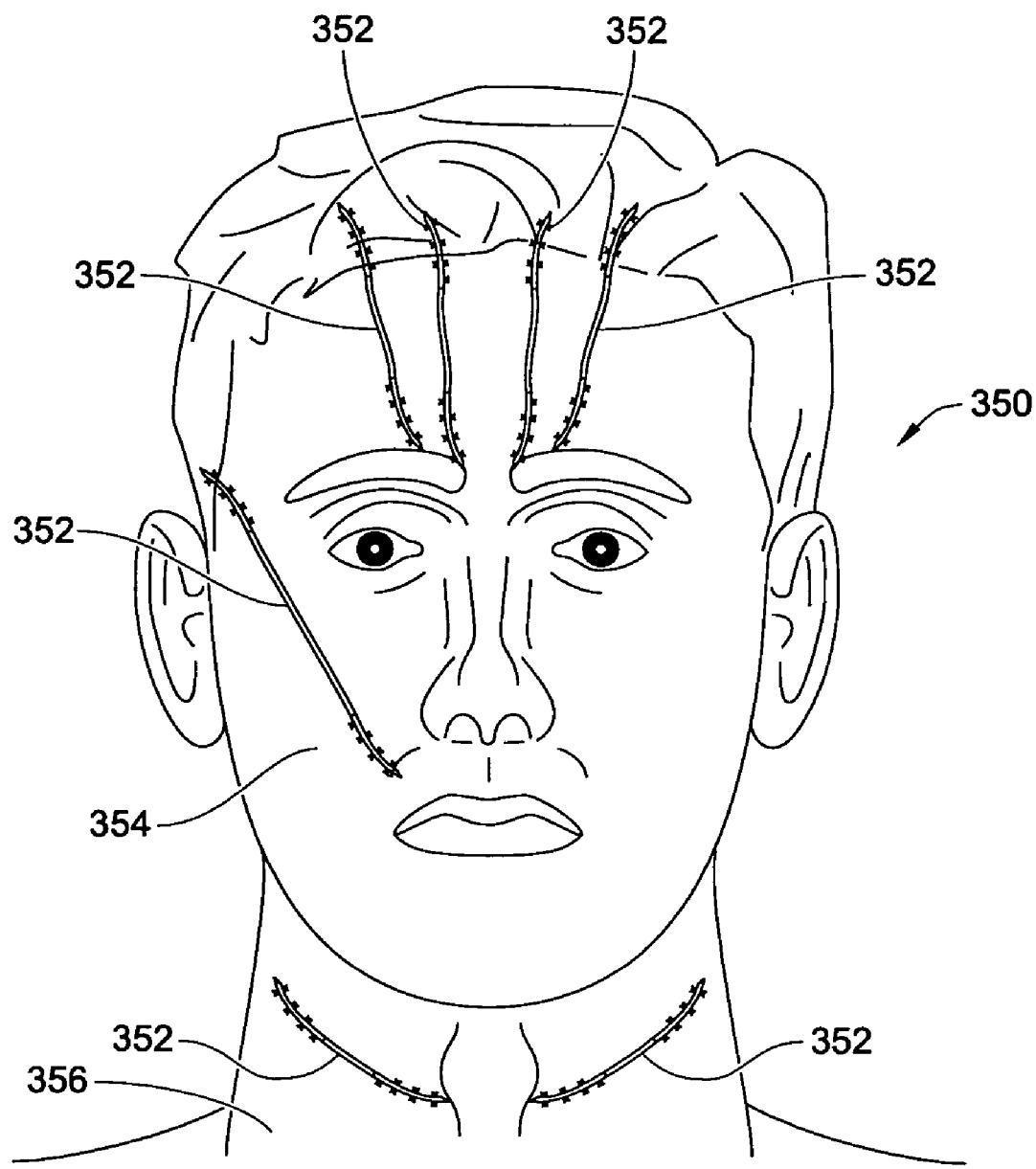
FIG. 18 is a front elevated view illustrating the use of tissue-connecting straps on a patient requiring facial plastic surgery or laceration repair.

Reference is made to FIG. 18, which illustrates a patient 350 with a series of wound closure devices 352 applied to the face 354 and neck 356 of the patient 350. The wound closure devices 352 can include any of the first, second or third embodiments of the present invention and can be attached to the surface of the face 354 or neck 356 of the patient 350, as illustrated, or below the surface, as described herein. While the illustration is described with respect to a wound closure device for wound repair, the device 352 can equally be used for plastic surgery, such as face or neck lifts. In this manner, one end of the wound closure device 352 can be securely placed at a desired location on the face 354 or neck 356. Tension can then be applied to the wound closure device 352 thereby lifting or pulling the skin of the patient 350. The other end of the wound closure device 352 can then be inserted into the skin fascia location and locked in place according to the methods described in this disclosure, thereby keeping the tension applied to the wound closure device addressing the skin of the face 354 or neck 356. While the wound closure devices 352 are described in FIG. 18 with respect to only the face 354 and neck 356 of the patient 350, the devices 352 have equal application throughout the patient's body.

Figure 19:
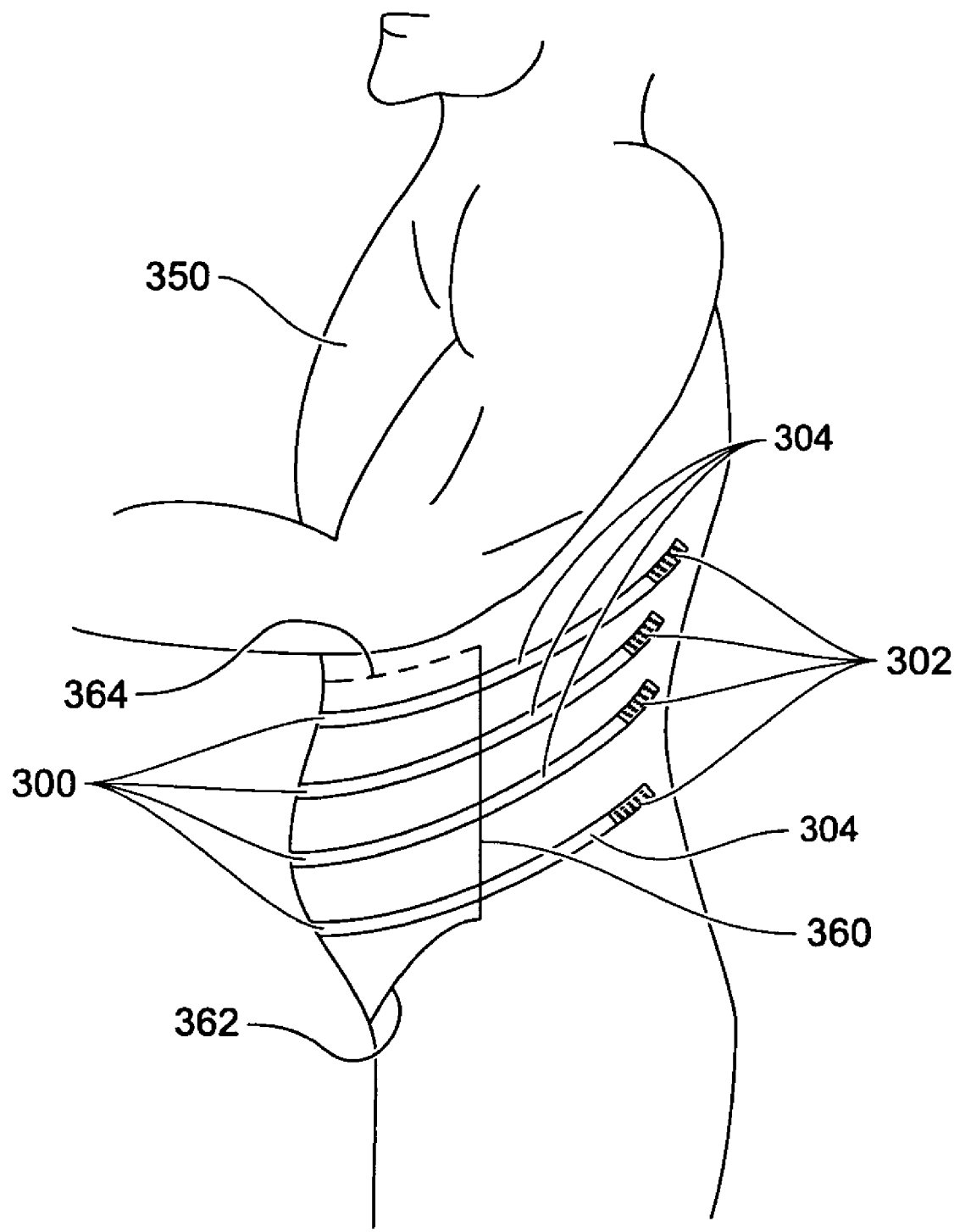
FIG. 19 is a side elevated view illustrating the use of multiple tissue-connecting straps of FIG. 16 in abdominal surgery and abdominoplasty.

Referring now to FIG. 19, the device of the present invention is illustrated in use to illustrate an abdominoplasty procedure. As illustrated in FIG. 19, the straps 300 are similar to those described and illustrated with respect to FIGS. 16 and 17 and comprise a tape 304 and tissue insertion tongues 302. In operation, the outer skin layer of the patient 350 is surgically removed along incision lines 360 and 362 and folded along fold line 364. One or more of the straps 300 can then be put in place as illustrated in FIG. 19 by placement of the tissue insertion tongue 302 on one side of the patient. The strap 300 is then placed along the stomach area of the patient as illustrated in FIG. 19, tension is applied to the strap 300 and then the tissue insertion tongue on the other end of the strap 300 is secured in the fascia on the other side of the patient. The tension action from the straps 300 lifts the stomach area for the end result. As with the embodiment shown in FIGS. 16-19, the strap 300 can be replaced by the device illustrated in the third embodiment of this disclosure.

The present invention also contemplates a wound closure device for connecting tissue comprising a strap having a ventral barbed surface. The device preferably has two parallel tiers of material, each tier having an end connected to the strap at a junction. The inner surface of each tier is ratcheted for releasable engagement with the connector of a second strap. This would allow for adjusting the two straps if it was accidentally pulled too tight. The straps ratchets can be disengaged by moving them perpendicular to the ratcheting direction in one or both perpendicular directions. Other versions could be fabricated such that no direction could disengage the two straps. Only permanently destroying the bond would disengage the straps.

The present invention also contemplates a wound closure system having two identical wound closure devices and an engagement tool. A preferred version has a tool engagement slot at the connector junction. The engagement tool has two triangular hooks for latching each of two engagement slots at the connector junction of each wound closure device. The pivots allow misaligned devices to come together and latch. The tool does not necessarily need to be triangular. The engagement tool "hooks" into each strap individually so the two straps can be pulled together. The tool finds the "engagement" slot in each device by pivoting on several axes. The pivots of the tool and the engagement slot allow misaligned closure devices to be pulled together. The closure devices do not have to be parallel to each other for the ratchets to hold. There is an angle in which the two straps will stay connected even though the ratchets are not in parallel engagement.

A repair device is also contemplated which comprises first and second anchor devices each having barbs for engagement with tissue, wherein a locking ring is attached to the first anchor device and a strip of material such as mesh or tape is attached to the second anchor device. In use, the anchors are set in tissue and the strip of material is threaded through the locking ring. Pulling or releasing a string attached to the strip of material may adjust the tension in the strip of material.

It is understood that the invention is not confined to the particular construction and arrangement of parts herein illustrated and described but embraces such modified forms thereof as come within the scope of the following claims.

What is claimed is:

1. A surgical fastener for connecting tissue, comprising:
a male connecting strap having a proximal end, a distal end opposing the proximal end, and a first tissue-connecting mechanism at the distal end; and
a female connector having a proximal end, a distal end opposing the proximal end, and an engagement clasp at the proximal end and a second tissue-connecting mechanism at the distal end, wherein the engagement clasp comprises a buckle for securing the male connection strap,
wherein the first tissue-connecting mechanism of the male connecting strap and the second tissue-connecting mechanism of the female connector each comprise an engagement clasp integrally connected thereto, the engagement clasp comprising a forked opening including an upper plate and a lower plate defining a cavity therein, wherein each of the first and second tissue-connecting mechanisms comprises at least one row of ratchets extending from the upper plate of the engagement clasp and at least one row of ratchets extending from the lower plate of the engagement clasp, wherein the ratchets are generally triangular in shape having a dorsal ridge ending in the cavity such that the dorsal ridge of the ratchets on the upper plate face the dorsal ridge of the ratchets on the lower plate.

2. The surgical fastener of claim 1 wherein the buckle comprises a rotating hinge bar including a post receptor wherein the hinge bar is rotatably connected to a receiving platform by a hinge wherein the receiving platform is defined by at least one post adapted to engage with the complementary post receptor.

3. The surgical fastener of claim 1, wherein the first and second tissue-connecting mechanisms are selected from the group consisting of ratchets, light curing epoxy including the entire electromagnetic spectrum from gamma rays, x-rays, ultraviolet, visible, infrared, microwave radio waves to ultra low frequencies for permanently or temporarily connecting the two straps; DC electrical curing epoxy for permanently or temporarily connecting two connecting straps; magnetic forces to bond the straps permanently or temporarily; ultrasonic energy to bond the straps permanently or temporarily; vibration energy to bond the straps permanently or temporarily; heat, including conduction, convection and radiation energy to bond straps permanently or temporarily; and adhesives, glues, epoxy using either a pressure force or a chemical reaction to bond the straps permanently or temporarily.

* * * * *